(12) United States Patent
Slemker et al.

(10) Patent No.: US 6,287,345 B1
(45) Date of Patent: *Sep. 11, 2001

(54) VALVE ASSEMBLY FOR A PROSTHETIC LIMB

(75) Inventors: Tracy C. Slemker, Clayton; Dennis E. Meyer, Montgomery County; Scott R. Schall, Englewood, all of OH (US)

(73) Assignee: The Ohio Willow Wood Company, Mt. Sterling, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/154,237

(22) Filed: Sep. 16, 1998

Related U.S. Application Data (63) Continuation-in-part of application No. 08/947,668, filed on Oct. 9, 1997, which is a continuation of application No. 08/516,557, filed on Aug. 18, 1995, now Pat. No. 5,702,489.

(51) Int. Cl.[7] .................................................. A61F 2/80
(52) U.S. Cl. ................... 623/34; 623/33; 623/38
(58) Field of Search ..................... 623/33, 34, 38, 623/35, 36, 37

(56) References Cited

U.S. PATENT DOCUMENTS

| | | | |
|---|---|---|---|
| 980,457 | * 1/1911 | Toles | 623/34 |
| 2,464,443 | 3/1949 | Ganoe et al. . | |
| 2,530,285 | * 11/1950 | Catranis | 623/34 |
| 2,533,404 | 12/1950 | Sharp et al. . | |
| 2,671,225 | * 3/1954 | Schoene | 623/33 |
| 2,696,011 | 12/1954 | Galdik | 3/17 |
| 2,790,180 | * 4/1957 | Hauser | 623/34 |
| 2,808,593 | 10/1957 | Anderson | 3/17 |
| 4,283,800 | 8/1981 | Wilson | 3/21 |
| 5,139,523 | * 8/1992 | Paton | 623/33 |
| 5,163,965 | * 11/1992 | Rasmusson | 623/36 |
| 5,376,129 | 12/1994 | Faulkner et al. . | |
| 6,063,125 | 5/2000 | Arbogast et al. . | |

FOREIGN PATENT DOCUMENTS

| | | | |
|---|---|---|---|
| 2729800 | 1/1979 | (DE) . | |
| 9418210 | 11/1994 | (DE) . | |
| 019612 | * 5/1980 | (EP) | 623/34 |
| 2069847 | 9/1981 | (GB) . | |
| 2087727 | 6/1982 | (GB) . | |
| 8400881 | 3/1984 | (WO) . | |

OTHER PUBLICATIONS

V.K. Pohlig, "Optimierung von Prothesenschäften mit dem Air Contact System (ACS)", Med. Orth. Tech., 114, pp. 272–276 (1994).

Supplemental European Search Report issued in European counterpart Application No. 96928214.4 (Nov. 1999).

United States Manufacturing Company "Suction Socket" Advertisement, first known publication date: Sep. 1, 1998, O&P Business News.

O & P Almanac "The Magazine for the Orthotic & Prosthetics Profession" Nov. 1997 pp. 12 & 19 Ohio Willow Wood Company "Alpha Suction Attachment Block System".

Endolite literature, The Endolite Flexible Socket Valve.

United State Manufacturing literature, "Super Seal" Valve System.

* cited by examiner

Primary Examiner—Michael J. Milano
(74) Attorney, Agent, or Firm—Oblon, Spivak, McClelland, Maier & Neustadt, P.C.

(57) ABSTRACT

A prosthetic limb comprises a socket for receiving a patient's residual limb, and an upright assembly. The socket includes a base provided in its distal end. The base includes a chamber therewithin and an channel for providing fluid communication between the chamber and the interior of the socket. A duct extends through the socket and engages the base such that it is in fluid communication with the chamber. A valve is coupled to the duct to allow controlled or forced gas transfer to and from the interior of the socket. A seal is provided between the base and the socket to facilitate suction between the patient's residual limb and the socket.

33 Claims, 8 Drawing Sheets

VALVE ASSEMBLY FOR A PROSTHETIC LIMB

CROSS-REFERENCE TO RELATED APPLICATIONS

This is a continuation-in-part of U.S. application Ser. No. 08/947,668 filed Oct. 9, 1997, which in turn is a continuation of U.S. application Ser. No. 08/516,557 filed Aug. 18, 1995, now U.S. Pat. No. 5,702,489.

BACKGROUND

The present invention relates generally to prosthetic devices and, more particularly, to a valve assembly for use with a prosthetic limb socket.

A prosthesis is often used to replace an amputated portion of a limb and to help restore the amputee's ability to use that limb. A prosthesis for a lower extremity amputation will often include an artificial foot connected to an upright assembly (pylon, tube or shaft) which is in turn connected to a custom fitted socket assembly (it is also known in the art to use non-custom fitted socket assemblies). If the amputation is an above-the-knee amputation, the upright assembly will commonly include an artificial knee joint.

An above-the-knee prosthesis typically requires two interlaying sockets; an inner socket consisting of a flexible, thermoplastic material, and a stronger, less flexible, thermoplastic outer socket which is attached to the upright assembly of the prosthesis. The inner socket is typically designed to interface with and cushion the amputee's residual limb, to protect the amputee's residual limb from the interconnection components which attach the socket assembly to the upright assembly, and to provide an air-tight seal between the residual limb and the outer socket.

This type of prosthesis is typically held on the patient by suction formed in the socket. Therefore, the inner socket will typically include a valve system positioned in the distal inner thigh portion of the socket assembly to release air trapped between the wearer's residual limb and the inner socket as the wearer is inserting the residual limb into the socket. After insertion of the residual limb in the socket, the valve system will be closed, thus forming the suction within the socket.

One typical valve system includes an annular valve housing permanently formed into a projection extending from the inner socket, and a valve which is usually threadedly engaged within a threaded hole in the annular valve housing. Such a valve system is typically constructed such that it protrudes from the inner socket through a hole in the outer socket to provide access to the valve system. Construction of the inner socket for this type of valve system typically includes the step of drape forming or blister forming a thermoplastic socket cone over a socket mold having the valve housing attached thereon. The valve housing will thus be vacuum formed or permanently laminated into the socket during fabrication of the socket. Excess plastic is then ground from around the valve housing to expose and facilitate access to the threaded hole in which the valve will engage. A valve can then be threadedly engaged into the valve housing such that gas may be transferred through the valve.

A disadvantage with such a fabricating process is that during the blister forming operation the plastic cone will catch on the fabrication plate and will periodically stretch thin in that area. Also, the transition from the inner surface of the socket to the valve can be very rough and uneven. Furthermore, because the valve housing is permanently molded into the socket, if there is a failure in the valve housing the entire inner socket may need to be re-fabricated.

Another typical valve system includes a valve housing comprised of two pieces. An annular housing member extending through the inner socket, having an annular flange for providing a seat and a seal against the inner surface of the socket; and an annular nut member which threadedly engages the outer circumference of the annular housing member extending from the inner socket. Once the nut member is threaded on the housing member, thus attaching the housing to the socket, a valve can then be threadedly engaged within the valve housing. Construction of the inner socket for this type of valve system will typically include the step of vacuum forming a thermoplastic preform cone over a positive cast of the amputee's residual limb having a definition-plate attached to the positive cast in the location of the vacuum housing. Once the socket is formed, a hole will be drilled into socket projection formed by the definition plate to facilitate insertion of the valve housing member.

A disadvantage with this type of valve system is that the thickness of the socket around the valve housing is unpredictable, and therefore, the fit of the valve housing within the socket will also be unpredictable.

An additional disadvantage with both valve systems described above is that, because of the inner thigh location of the valves, when the residual limb is inserted into the sockets the valve systems do not release air directly from the distal end (or bottom) of the sockets. The distal end of the limb may cover and seal off the valves in the sockets before the limb can be completely inserted into the sockets, preventing air from being released from the sockets. This may result in an undesirable air pocket between the distal limb and the distal end of the sockets.

Another disadvantage with the above valve systems is the requirement of the two sockets. Besides the added time and expense of creating an inner socket in the first place, if the inner socket needs to be re-fabricated due to damage or needs to be re-fitted due to a change in the limb dimensions, the hole on the outer socket for the valve may no longer align with the valve projection protruding from the inner socket. Furthermore, two sockets can give the prosthesis a long profile; thus if the amputation is immediately above the knee, the prosthesis may undesirably extend the thigh portion beyond where the knee joint should be.

Yet another disadvantage with the above valve systems is that the valve systems do not facilitate the forced suction of gas from, or the forced injection of gas into the socket. Oftentimes the volumetric dimensions of the residual limb will change within a very short period of time due to fluid retention or fluid loss. A volumetric loss can result in socket retention problems, which could be corrected using forced suction. A volumetric gain can result in the residual limb being mechanically locked into the socket; and removal of the socket in such an instance could be greatly assisted using forced air injection.

Accordingly, a need exists for an improved valve system which will reduce the amount of skill, time, and equipment needed to fabricate or replace a prosthesis. A need exists for a valve system which helps to reduce the levels of variance in the socket fabrication processes. A need exists for a valve system which facilitates easier donning of the prosthesis by reducing time and effort required by the amputee to attach the prosthetic limb to the residual limb. Furthermore, a need exist for a valve system which facilitates forced suction and forced injection of air from and into the socket.

SUMMARY OF THE INVENTION

The present invention is a valve assembly for a prosthetic limb which responds to the problems associated with the prior prosthetic limb devices and valve systems. More particularly the present invention provides a cylindrical or hemispherical valve plate for insertion into the distal end of a prosthetic limb socket. In a preferred embodiment the present invention is used with the interface connector disclosed in U.S. Pat. No. 5,662,715, the disclosure of which is hereby incorporated by reference.

In accordance with the present invention, the valve assembly includes a base which is fitted within the distal end of the socket. The base includes a chamber therewithin and an channel extending through the proximate surface of the base for providing fluid communication between the chamber and the interior of the socket. The valve assembly also includes a duct extending through the socket engaged with the base, which is in fluid communication with the chamber. A valve is coupled to the duct outside of the socket and an air tight seal is provided between the base and the socket so that a suction fit can be achieved as described below.

In a preferred embodiment an interface cushion member is mounted in the distal end of the socket and engaged with the base. The cushion includes a cavity which opens on its distal end and a projection extending radially around the mouth the cavity such that the base is retained in the cavity by the projection. The cushion member also includes at least one channel extending therethrough which provides fluid communication between the cushion member cavity and the interior of the socket. The projection of the cushion member includes a passage through which the duct extends and also provides the air tight seal between the base and the socket.

In the above preferred embodiment the base further includes a means for releasably attaching the base within the socket and means for releasably attaching the prosthetic limb upright assembly to the distal end of the socket. The cushion member preferably includes a substantially concave proximate surface which has a flexible feathered periphery extending radially outward from the surface, such that the interface cushion is adapted to abut the amputee's residual limb and such that the transition from the inner surface of the socket to the approximate surface of the interface cushion is substantially smooth without wrinkles or creases.

In operation, as the amputee's residual limb is inserted into the socket, the excess air escapes from within the socket through the valve assembly in the distal end of the socket. Once the residual limb is inserted comfortably within the socket the valve is closed, forming a suction such that the socket will be secured to the amputee's residual limb.

Alternatively, a quick-disconnect port on the valve could be utilized to force suction from, or inject gas into, the socket. Therefore, the forced transfer of air could correspondingly assist in the donning and removal of the prosthesis to and from the patients residual limb.

DETAILED DESCRIPTION

Figure 1:
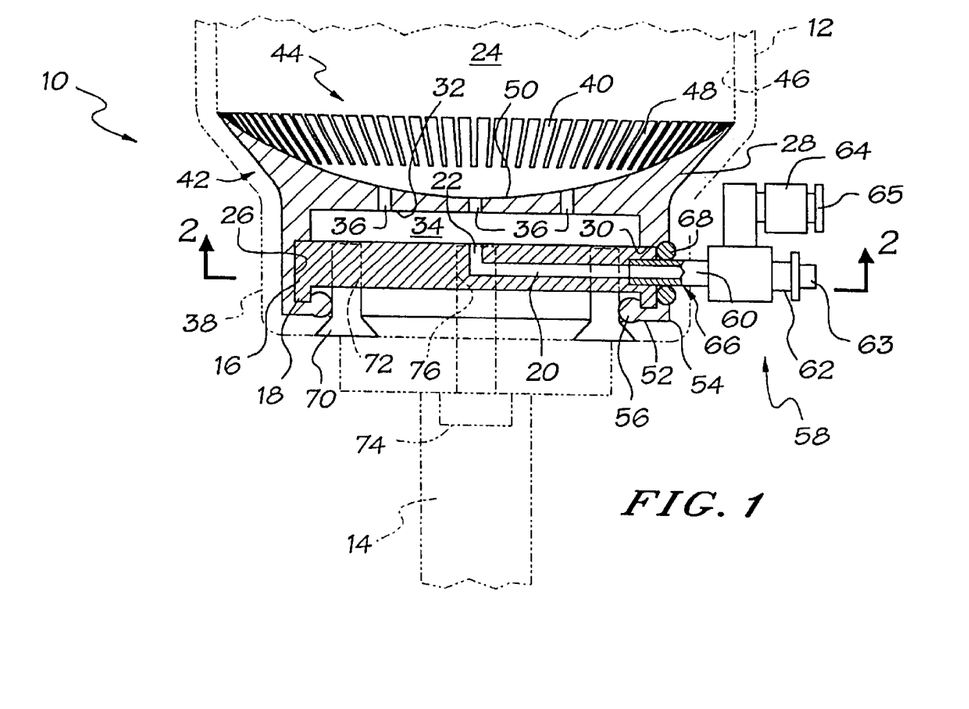
FIG. 1 is a cross-sectional view of a first embodiment of a valve assembly of the present invention.
Figure 2:
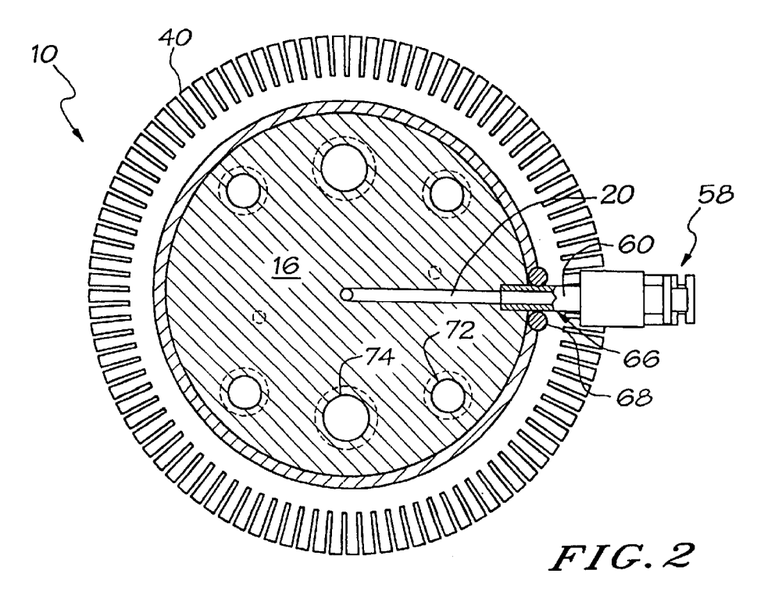
FIG. 2 is a cross-sectional view taken along lines 2—2 of FIG. 1.

As shown in FIG. 1 a first embodiment of the valve assembly of the present invention, generally depicted as 10, is used to facilitate the donning and removal of the prosthetic limb on a patient's residual limb. In a preferred embodiment, the valve assembly is also used as a interface connector for connecting an upright assembly 14 to a distal end of a prosthetic limb socket 12.

The preferred embodiment of the valve assembly 10 includes a cylindrically shaped stainless-steel base plate 16 having an annular rim 18 extending distally from the periphery of the base plate 16. The base plate 16 includes an inner chamber 20 existing therewithin and an channel 22 which provides fluid communication between the socket interior 24 and the inner chamber 20.

It is noted that although the base is preferably substantially cylindrically shaped, other shapes adapted to fit the base within a distal end of the socket will suffice. For example, it is within the scope of the invention that the base be substantially hemispherically shaped, such as to fit the base within a cup-shaped distal end of a socket. Similarly, the base can be constructed of any rigid, non-permeable material or materials in place of the preferred stainless-steel material.

Preferably, an interface cushion 28 is mounted over the base plate 16 by inserting the base plate 16 within a cylindrical cavity 26 existing in a distal end of the interface cushion 28. The cavity 26 has an annular shoulder 30 which prevents the base plate 16 from abutting a proximate surface 32 of the cavity 26 such that the base plate 16 is retained in the cavity 26 to form an intermediate air chamber 34 between the base plate and the interface cushion. The interface cushion 28 includes a plurality of channels 36 to provide fluid communication between the socket interior 24 and the intermediate air chamber 34. It also is within the scope of the invention to fill the intermediate air chamber 34 with a removable porous pad (not shown), to provide additional cushioning.

The interface cushion 28 is shaped to fit within a distal socket extension 38 of the socket 12; however, it also is within the scope of the invention that the interface cushion be adapted to fit within a distal end of a socket not having a socket extension. The interface cushion is preferably made from a thermoplastic polyurethane such as Santaprene (a registered trademark of Monsanto Corporation). It is also within the scope of the invention to construct the interface cushion from any flexible material capable of providing sealing capabilities required from the invention as described below.

In the preferred embodiment, the interface cushion 28 has a multitude of tapered blades 40 extending from the outer periphery of the proximate end 42 of the interface cushion, giving the interface cushion a flexible feathered periphery 44 which conforms to the inner surface 46 of the socket 12 when the interface cushion is inserted into the socket extension 38. The proximate surfaces 48 of the blades are flush with a concave proximate surface 50 of the interface cushion. The feathered periphery 44 allows the concave proximate surface 50 of the interface cushion to smoothly transition into the inner surface 46 of the socket, substantially without the formation of creases or wrinkles.

An annular shoulder 52 extends radially inward from an outer rim 54 of the cavity 26, and projects over the annular rim 18 of the base plate 16 to retain the base plate 16 within the cavity 26. An annular o-ring projection 56 extends radially inward from the shoulder 52 and engages the rim 18 to form an air-tight seal between the base plate 16 and the socket 12.

A valve 58 having a valve duct 60 extends through the socket 12 and is engaged with the base plate 16 such that the duct 60 is in fluid communication with the base plate chamber 20. The valve duct 60 extends through a passage 66 in the interface cushion and an air-tight seal 68 is provided to seal the duct from the socket. Preferably, the valve has two ports, an open/close or needle-valve port 62 and a quick disconnect port 64. Such a flow control valve is commercially available from SMC Corporation, Tokyo, Japan, as a "Series AS" Direct Connection Type, Speed Controller With One-touch Fittings.

The open/close port 62 operates as follows: rotating or screwing a needle-valve handle 63 on the open/close port 62 clockwise closes the valve, and rotating the handle 63 counter-clockwise opens the valve. The quick-disconnect port 64 operates as follows: to attach a pump tube (not shown), a release bushing 65 is pulled out to an unlock position and the pump tube is inserted in the port 64. By releasing the bushing 65, the bushing returns to the locked position, and the pump tube becomes locked into the port. At this point, the pump is then able to either inject gas through the valve 58 into the socket, or to suck gas through the valve 58 from the socket. To remove the pump tube, the bushing 65 is again pulled out to the unlock position, which allows the pump tube to be taken from the port.

It is noted that although the valve 58 described above is preferred, it is within the scope of the invention to provide a valve having only one of the two types of ports, and it is also within the scope of the invention to alternatively utilize any valve mechanism which allows and/or forces the transfer of gases to and from the prosthetic limb socket. The valve 58, or one of the valve ports, could alternatively be the type of valve which allows the transfer of gas in only one direction. Such a valve is conventionally known as a leakrate valve or a check valve. This type of valve could be configured to allow gas to be released from the socket while simultaneously restricting gas from being sucked back into the socket. This would help to enhance the suction fit of the socket on the patients residual limb.

The valve plate assembly 10 is releasably attached in the socket extension 38 by four screws 70 extending through holes in the distal end of the socket and engaged by threaded holes 72 in the base plate 16. The upright assembly 14 is releasably attached to the distal end of the socket by two bolts 74 extending from the upright assembly, through holes in the distal end in the socket and engaged by threaded holes 76 in the cylindrical base plate 16. In the present embodiment, the bolts and screws must be sealed to avoid leakage through their respective holes, using a silicone seal or a commercially available product known as "242 Loctite."

It is within the scope of the invention that the bolts 74, or similar attachment means, can be used to attach the upright assembly 14 to the socket 12 and the base plate 16 within the socket 12, without the need for additional attachment means. The valve assembly 10 can also be either permanently or temporarily bonded into the socket by use of epoxy or hook and pile mechanisms, or any other known means for such an attachment.

The first embodiment of the invention operates as follows. Before the patient inserts his or her residual limb into the socket, it is preferred that the patient roll a silicone sleeve over the residual limb. The silicone sleeve helps protect the limb and provides a seal between the limb and the socket when the limb is tightly fitted in the socket. It is noted here that even though a silicone sleeve is preferred, the present invention is especially designed to allow the patient to don a prosthetic limb without having to wear any external sleeve at all; although it is preferred that the patient at least apply some sort of lubrication to the residual limb facilitate in donning and removal of the prosthesis. With or without an added sleeve, the combination of the interface cushion and the valve plate will simultaneously lock the patient's residual limb in the socket and will suitably protect and comfort the limb in the socket.

Before inserting his or her limb into the socket, the patient will first set the valve port 62 to the open position. At this valve setting the residual limb can be easily inserted into the socket 12 and the excess air will be forced through the valve plate assembly 10 and out through the open valve port 62. Once the residual limb is inserted comfortably in the socket 12, against the concave surface 50 of the interface cushion 28, the patient then closes the valve port 62. Thus, because of the seals provided by the invention 56, 68, suction is formed which secures the patient's residual limb within the socket, and the distal position of the valve plate assembly guarantees that substantially no air pockets are left between the patient's residual limb and the interface cushion 28.

To remove the residual limb from the socket the valve port 62 is opened again thus breaking the seal and allowing air to be brought into the socket through the valve plate assembly such that the residual limb can be easily removed from the socket.

The quick-disconnect port 64 of the valve provides an alternate means for the patient to insert or remove his or her residual limb from the socket 12. A pump mechanism may be attached to this quick disconnect port so as to force suction from or to force gas injection through the valve. Such a mechanism can be as simple as a hand-held pump, or it can be an electronically or hydraulically controlled device. To facilitate donning of the prosthetic limb, the residual limb will be inserted into the socket and the hand-held air pump is inserted into the quick disconnect port. The pump is then operated to suck the air from the socket and simultaneously suck the patient's limb into the socket. When the patient wishes to remove the residual limb from the socket, the pump is again inserted into the quick disconnect port and the pump is operated to inject air into the socket thus forcing the patient's residual limb from the socket.

Figure 3:
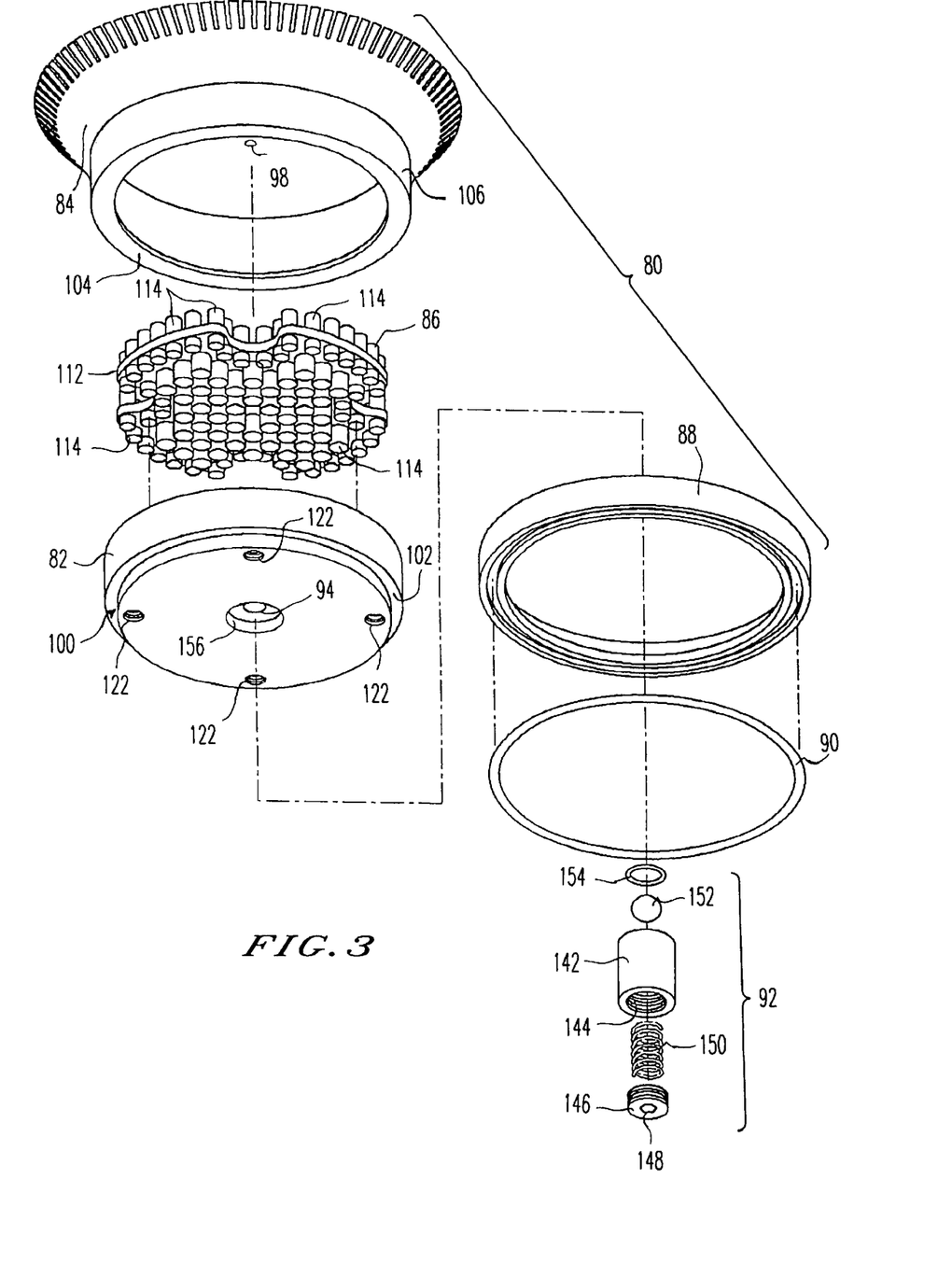
FIG. 3 is an exploded, perspective view of a second embodiment of a valve assembly of the present invention.
Figure 4:
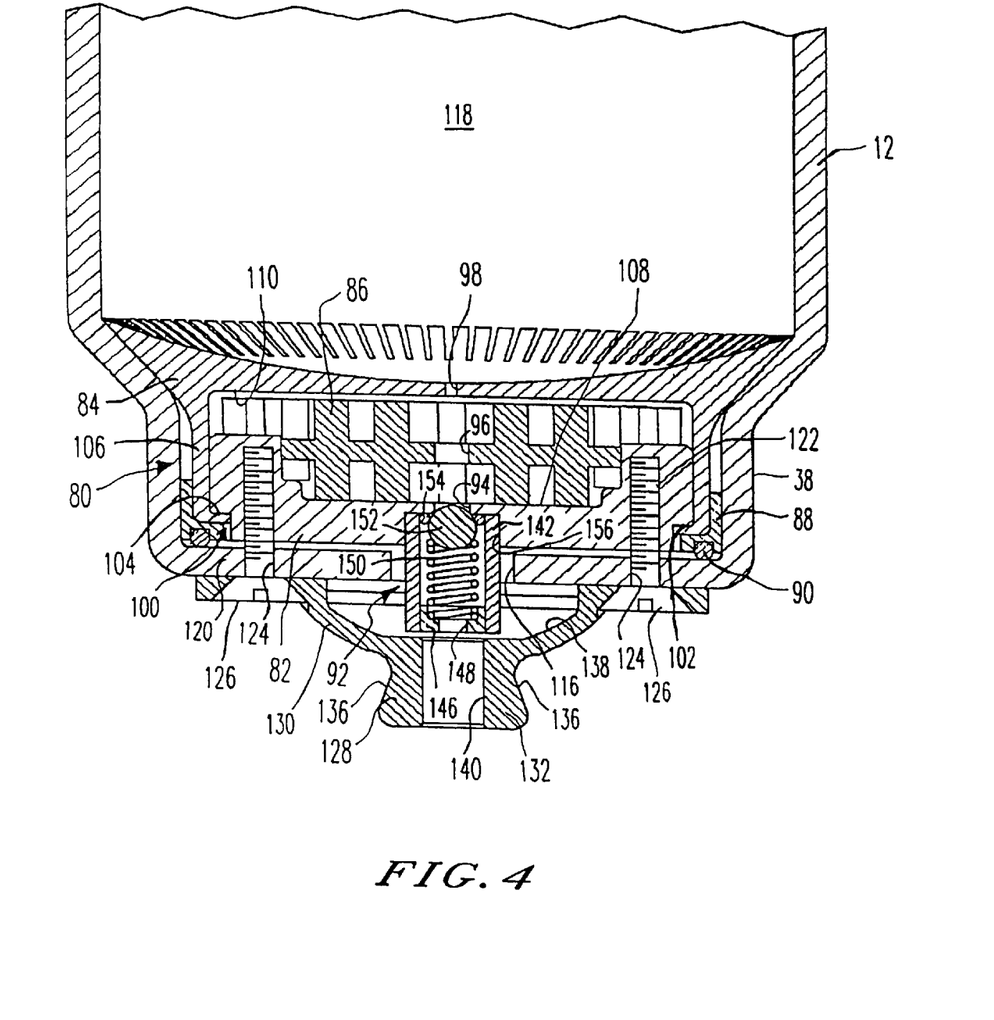
FIG. 4 is a cross-sectional view of the valve assembly of FIG. 3, mounted within a prosthetic limb socket.

As shown in FIGS. 3 and 4, a second embodiment 80 of the present invention includes a substantially disk-shaped base plate member 82, an interface cushion member 84 carried on and extending proximally from the base plate member, a porous pad member 86 positioned between a proximal surface 110 of the base plate member 82 and a distal surface of the cushion member 84, an annular O-ring bracket carried on a distal end of the cushion/cylindrical base plate assembly 84/82, an O-ring component 90 carried on a distal end of the O-ring bracket 88 and a check valve 92 mounted to the distal end of the cylindrical base plate component 82. The check valve 92 is in fluid communication within a channel 94 extending axially through the base plate component 82, a channel 96 (see FIG. 4) extending axially through the porous pad component 86 and a channel 98 extending axially through the interface cushion component 84. The cylindrical base plate component 82 includes an annular notch 100 formed into the outer distal periphery thereof so as to provide an annular shoulder 102 adapted to seat a radially inwardly extending flange 104 extending from a distal end of a distally extending cylindrical projection 106 extending from the interface cushion member 84. The cylindrical base plate component 82 also includes a recess 108 extending into its proximal end for seating the porous pad component 86 therein. The length of the cylindrical extension 106 is preferably such that s cavity is formed between the proximal end of the cylindrical base plate component 82 and a distal surface 110 of the interface cushion component 84.

The porous pad component 86 is adapted to fill this cavity created between the interface cushion component 84 and the cylindrical base plate component 82. The porous pad component 86 is a flexible and resilient member preferably molded from a highly-flexible and resilient material such as Santeprene. The porous pad component includes a horizontally planer section 112 and a plurality of cylindrical nodules 114 extending vertically from both the proximal and distal surface of the planer member 112 and uniformly dispersed thereabout. The cylindrical nodules 114 include gaps between them so that air is able to easily move through and around the porous pad component, yet the nodules also provide the added cushioning and comfort for the patient's residual limb.

As shown in FIGS. 3 and 4, the O-ring bracket 88 is an annular bracket having a substantially L-shaped cross section so as to provide a seat for the radially inwardly extending flange 104 of the interface cushion 84. When assembled, the valve plate assembly 80 of the present embodiment is inserted into a prosthetic limb socket 12 and into a cylindrical socket extension 38 formed into the distal end of the socket. The socket extension 38 includes a channel 116 extending axially therethrough so as to allow the check valve 92 to extend out from the socket interior 118. The O-ring member 90 abuts the horizontally planer distal end 120 of the socket extension 38. The cylindrical base plate member 82 includes a plurality of tapped holes 122 extending vertically therein from a distal end of the cylindrical base plate member, and the distal end 120 of the socket extension 38 includes a plurality of non-threaded holes 124 aligned with the tapped holes 122. Accordingly, set screws are threaded from the distal end of the socket extension 38 through the holes 124 and into the tapped holes 122 of the base plate member, and when the set screws 126 are tightened against the distal end of the socket extension 38, the base plate member 82 is drawn in a distal direction, pressing O-ring 90 carried thereon against the inner surface of the socket extension 38 at the distal end 120 of the socket to as to create an air-tight seal between the valve plate assembly 80 and the distal end of the socket extension 120. The same set screws 126 used to secure the present embodiment 80 of the valve plate assembly are also used to retain a pyramidal-link plate component 128 of an upright assembly to the distal end of the socket.

As shown in FIG. 4, the pyramidal plate component 128 includes a domed portion 130 extending distally therefrom frustopyramidal boss portion 132 extending from the apex of the domed portion 130. The domed and frustopyramidal boss portions are of conventional design and adapted to be received within an annual socket member extending from a distal end of the pylon assembly (not shown). The annual socket member includes a spherically concave distal edge having substantially the same radius of curvature as the domed portion of the pyramidal link plate member 128. The frustopyramidal boss portion 132 includes a plurality of outwardly angled faces 136 for receiving proximally angled set screws (not shown) extending radially inward through the annual socket member. Once the set screws are tightened against their respective, outwardly angled faces 136 of the frustopyramidal boss portion 132, the pylon assembly will be locked in the desired orientation with respect to the pyramidal link-plate member 128. (See U.S. Pat. No. 3,659, 294 to Glabiszewski.)

The pyramidal link-plate member 128 of the present invention has been modified to receive the check valve 92 and to also allow the air within the socket interior 118 to be transferred out through the valve-plate assembly 80 and the check valve 92 to the ambient. Such modifications include a concave recess 138 extending into the proximal surface of the pyramidal-link plate member and a channel 140 extending axially through the first pyramidal boss portion 132 and in fluid communication with the concave recess 138.

Referring to FIGS. 3 and 4, the check valve includes a cylindrical tube 142 having a channel 144 extending axially therethrough, which is threaded at its distal end so as to receive a correspondingly threaded set screw 146 at a distal end thereof, where the threaded set screw 146 includes an air channel 148 extending axially therethrough. The proximal end of the set screw 148 is counter-bored to seat a spring 150, which in turn receives a metal ball 152 on its proximal end. Finally, carried on the proximal end of the metal ball is an O-ring component 154. When no air pressure is being applied to the proximal end of the metal ball 152, the force of the spring 150 presses the metal ball and O-ring member 154 proximally against the mouth of the channel 94 extending through the cylindrical base plate component 82, forming an air-tight seal between the ball 152 and the base-plate component 82. When substantial air pressure is applied against the proximal end of the ball 152, the ball is forced distally against the force of the spring 150 which allows air to pass between the ball 152 and the O-ring 154 and thereafter allows the air to pass through the cavity 154 and out through the channel 148 in the set screw.

The cylindrical base plate member 82 preferably includes a cylindrical recess 156 counter-bored into the distal end thereof and co-axially aligned with the channel 94 extending therethrough. The cylindrical tube 142 of the check valve 92 is press fit within the cylindrical recess 156. It is also within the scope of the invention that the base plate member 82 and the cylindrical tube 142 of the check valve 92 be a unitary member milled or formed from a single piece of material.

In operation, the valve plate assembly 80 of the present embodiment is inserted into the socket extension 38 at the distal end of the socket 12 and the set screws 126 are used to couple the pyramidal-link plate member 128 to the distal end 120 of the socket extension and to also draw the valve-plate assembly 80 distally against the proximal end 120 of the socket extension 38, thereby causing the O-ring component 90 to form an air-tight seal between the valve plate assembly 80 and the distal end 120 of the socket extension. Next, the wearer will insert his or her residual limb into the socket interior 118 through a proximal mouth of the socket (not shown) and will press downwardly so as to force his or her prosthetic limb distally into the socket interior 118, which in turn causes the air within the socket interior to be forced through the channel 98 in the interface cushion component 84, through the channel 96 in the porous pad component 86 and against the inlet of the check valve 92. Sufficient air pressure caused by the insertion of the prosthetic limb into the socket interior 118 causes the check valve to open and allows air to pass out of the socket interior 118, through the check valve 92, through the channel 140 in the pyramidal link plate member 128, and thereafter to the ambient. Once the prosthetic limb is securely received within the socket, the absence of any further air pressure against the metal ball 152 causes the check valve 92 to close, which in combination with the seal provided by the O-ring component 90, forms a vacuum within the socket interior 118 which acts to retain the residual limb within the socket 12.

Figure 5:
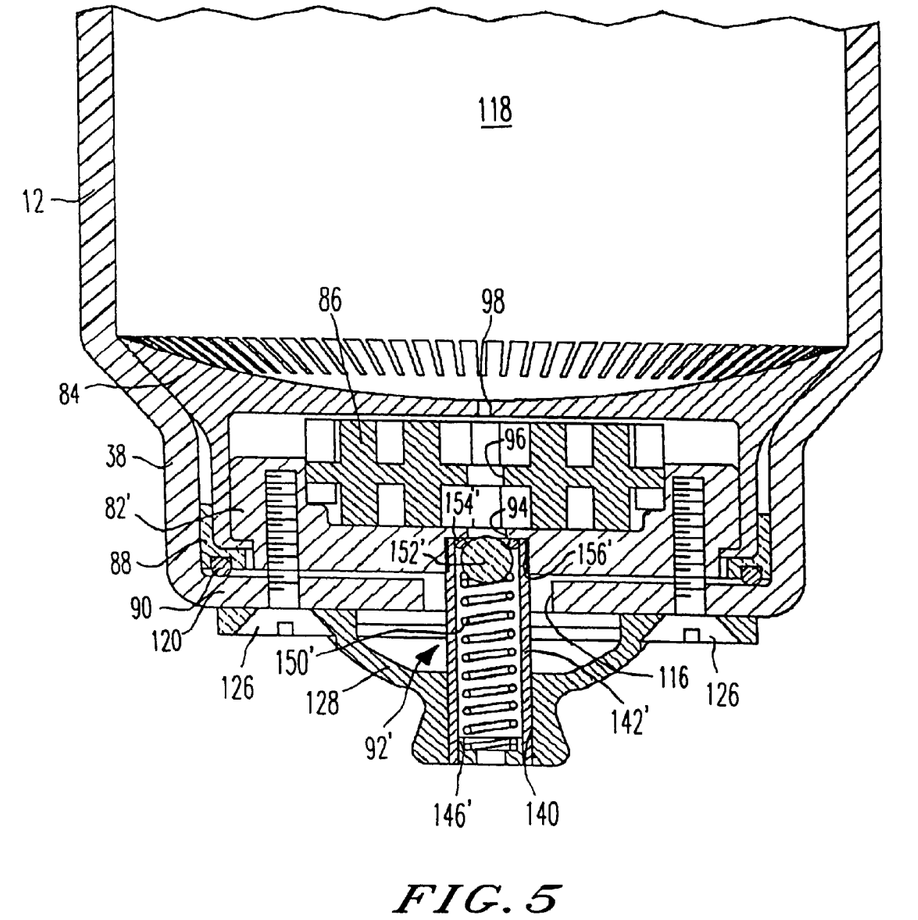
FIG. 5 is a cross-sectional view of a modified version of the valve assembly of FIGS. 3 and 4.

As shown in FIG. 5, an alternate design for the check valve 92' includes a cylindrical tube 142' having a threaded outer surface at its proximal end which is threaded into a correspondingly threaded inner surface of the cylindrical recess 156' extending into the distal end of the cylindrical base-plate member 82'. The cylindrical tube 142' extends distally through the opening 116 in the distal end 120 of the socket extension 38 and into the axial channel 140 of the pyramidal-link plate member 128.

Figure 6:
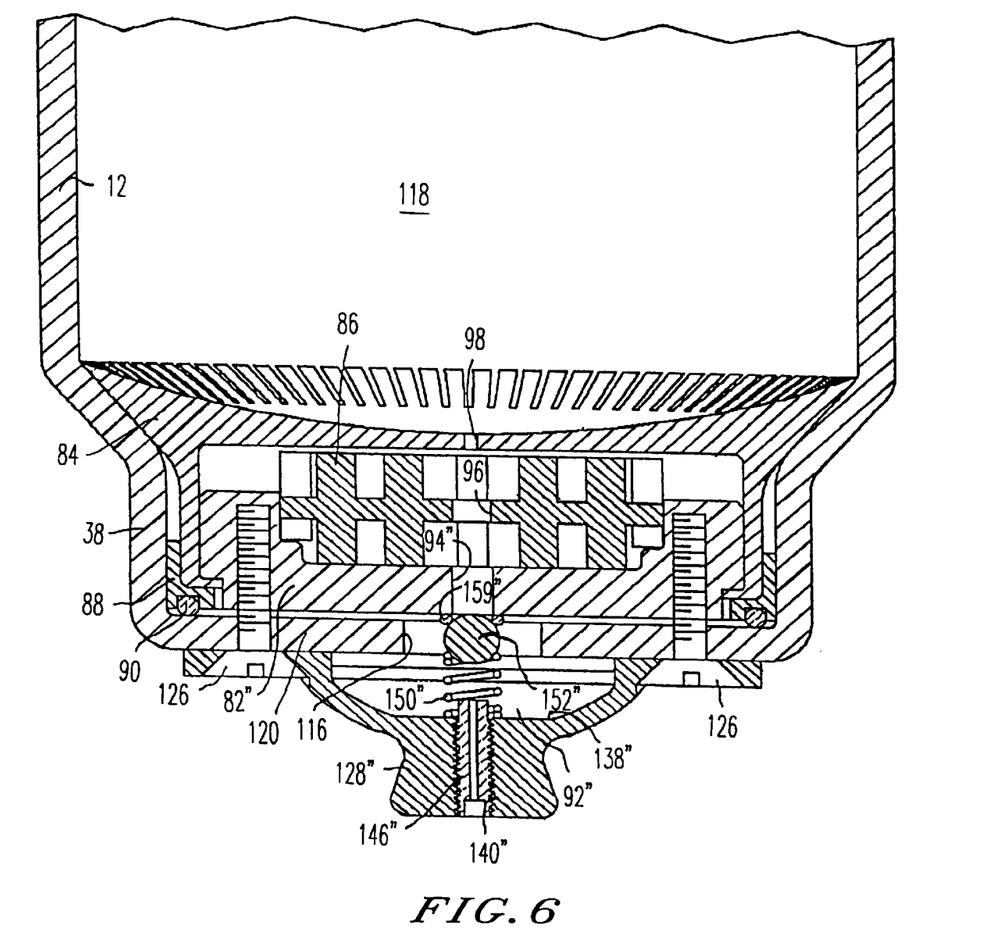
FIG. 6 is a cross-sectional view of another modified version of the valve assembly of FIGS. 3 and 4.

FIG. 6 provides yet another alternate design for the check valve 92" that does not include the cylindrical tube at all. In this embodiment, the axial bore 140" extending into the pyramidal link plate member 128" is tapped so as to receive a correspondingly threaded set screw 146". The set screw 146" has a channel extending axially therethrough to permit the transfer of air. The proximal end of the set screw extends inwardly into the concave recess 138" of the pyramidal link plate member so as to provide a seat for the spring member 150". As with the previous two embodiments, the check valve includes a metal ball 152 forced against a metal ball 152" riding on the proximal end of the spring 150" and an O-ring component 154" riding on a proximal end of the metal ball 152" so that the force of the spring 150" presses the ball 152" against the O-ring component 154" so as to provide an air-tight seal between the metal ball 152" and the axial channel 94 extending through the cylindrical base plate member 82".

While the embodiments illustrated in FIGS. 3–6 utilize a ball-and-spring type check valve, it is within the scope of the invention to use any other sufficient design for the check valve, such as a duck-bill valve, as will be apparent to those of ordinary skill in the art.

Figure 7:
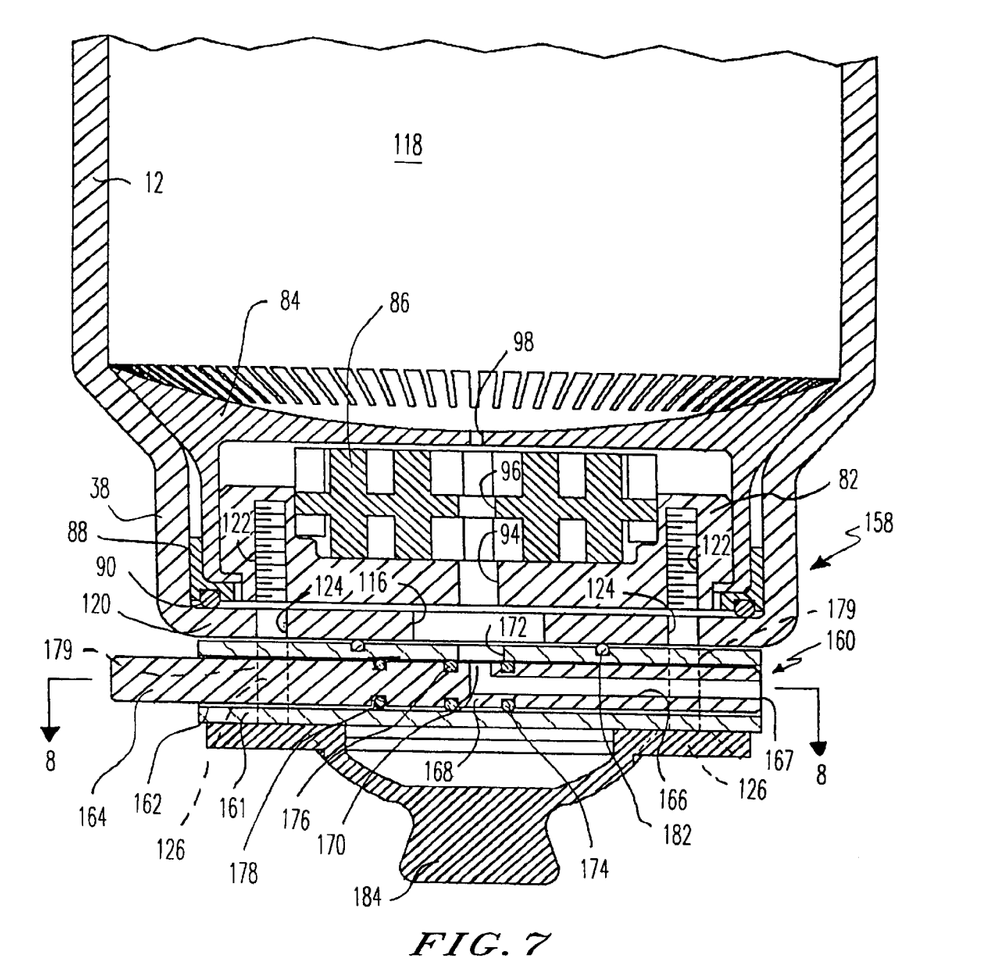
FIG. 7 is a cross-sectional view of a third embodiment of a valve assembly of the present invention, in its "open" orientation and mounted to a prosthetic limb socket.
Figure 8:
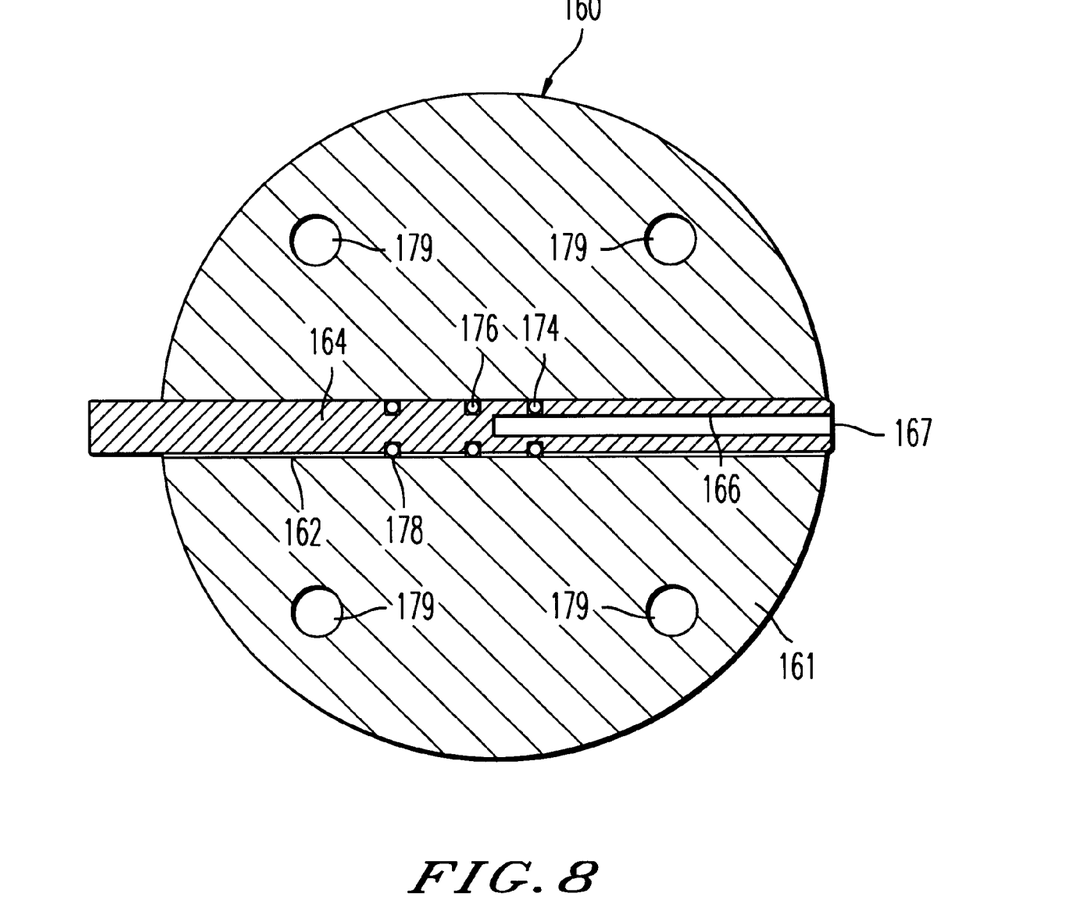
FIG. 8 is a cross-sectional view of the embodiment of FIG. 7 taken along lines 8—8 of FIG. 7.
Figure 9:
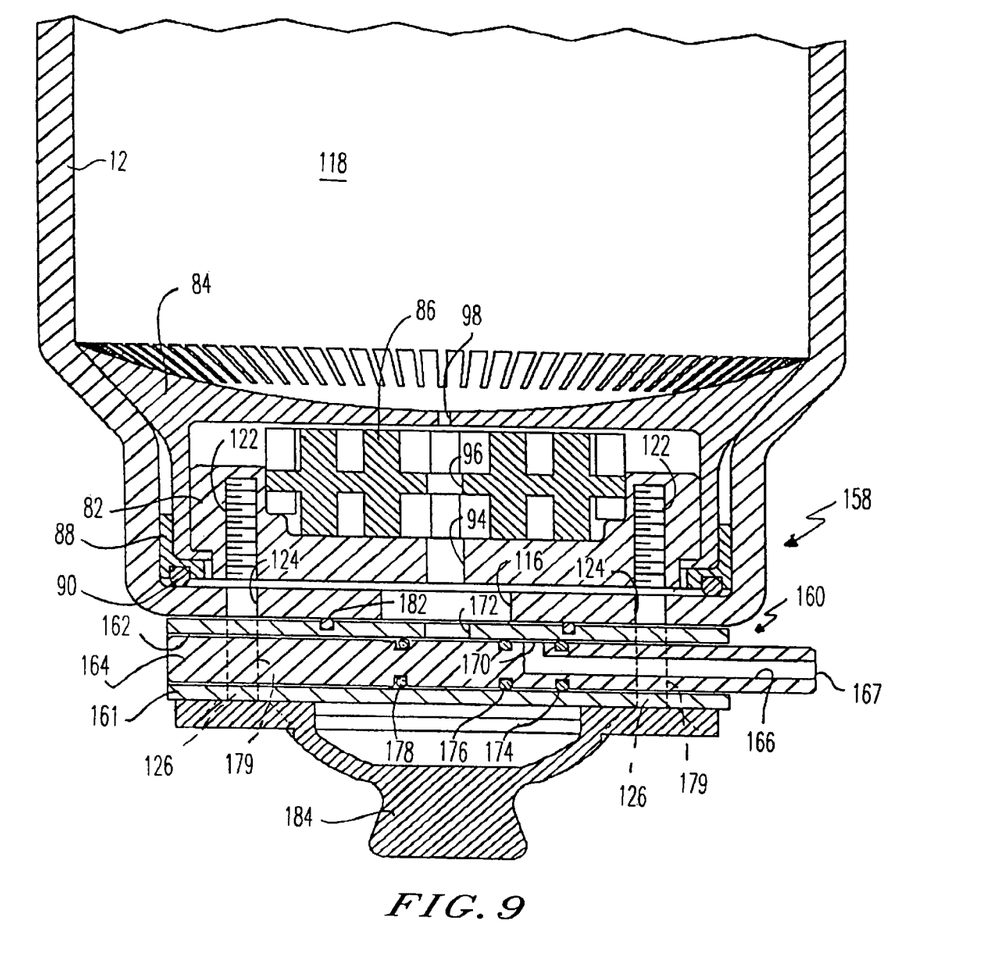
FIG. 9 is a cross-sectional view of the embodiment of FIG. 7 shown in its "closed" orientation.

As shown in FIGS. 7–9, a third embodiment 158 of the present invention provides a valve plate component 160 coupled to the distal surface of the distal end 120 of the prosthetic limb socket 12. The valve plate component 160 includes a cylindrical disc-member 161 having a cylindrical channel 162 extending diametrically therethrough, and also includes an air-transfer stem 164 slidingly received within the channel 162. The air-transfer stem 164 includes an air channel 166, having a first opening 167 at a longitudinal end thereof and a second opening 170 through a circumferential surface thereof, somewhat midway along the length of the stem. The channel 166 extends axially from the first opening 167 to a substantially central point 168 where it makes a 90° turn and thereafter extends in a radial direction out through the second opening 170. This second opening 170 is vertically oriented.

The disc-member 161 includes a central opening 172 extending into its proximal surface and providing fluid communication between the proximal surface of the disc-member 161 and the inner cylindrical channel 162. The air tube 64 is laterally slidable within the channel 162 from a first position (shown in FIG. 7) where the second opening 170 is aligned with the central opening 172 of the disc member 161 (allowing air to flow from the central opening of the disc member 172 out through the first opening 167 in the air-transfer stem) to a second position (shown in FIG. 9) where the second opening 170 is slid out of alignment with the opening 172 in the disc member such that air is unable to flow from the central opening of the disc member 172 out through the first opening 167 in the air-transfer stem. The air tube 164 includes a first annular notch receiving a first O-ring 174 on a first side of the second opening 170 and a second annular notch receiving a second O-ring 176 on an opposite side of the second opening 170. Accordingly, in the first position, as shown in FIG. 7, the O-rings 174 and 176 provide an airtight seal between the disc component 161 and the air-transfer stem 164. A third annular notch carries a third O-ring component 178 therein such that in the second position of the air-transfer stem 164 (as shown in FIG. 9), the O-ring components 176 and 178 form airtight seals between the disc member 161 and the air tube member 164 such that air will not leak from the interior of the prosthetic lim 118 out through the first opening 167 in the air-transfer stem 164.

The disc member 161 includes a plurality of through holes 179 extending therethrough which are aligned with the holes 124 in the distal end of the socket and the tapped holes 122 in the base plate member 82 such that set screws 126 can extend upward therethrough to couple the valve plate member 160 to the distal end of the prosthetic limb socket. The proximal surface of the disc member 161 includes an annular notch surrounding the central opening 172 that receives an O-ring member 182 therein. The O-ring member 182 provides an airtight seal between the valve plate component 160 and the distal end of the prosthetic limb, surrounding the central opening 172 of the disc-member 161 and the distal opening 116 of the prosthetic limb socket.

Finally, a pyramidal link plate member 184 may also be coupled to the distal end of the valve plate component 160 by the set screws 126 so as to facilitate connection of the present embodiment 158 to a pylon or upright assembly.

In operation, for a wearer don the prosthetic limb utilizing the present embodiment 158, the wearer will first slide the air-transfer stem 164 into the open position as shown in FIG. 7 and will then push his or her residual limb into the socket interior 118 such that air inside the socket interior will be forced out through the opening 98 in the interface cushion member 84, through the opening 96 in the porous pad 86, through the opening 94 in the cylindrical base plate member 82, out through the opening 116 and the distal end of the prosthetic limb socket, through the central opening 172 in the disc member 161 of the valve plate component 160, through the air channel 166 in the air-transfer stem 164, and out through the first opening 167 to the ambient. Once the patient's residual limb is secured within the socket, the patient will slide the air-transfer stem 164 to the closed position as shown in FIG. 9 such that a suction seal is formed within the socket interior 118, thereby retaining the patient's residual limb within the socket. When the patient wishes to remove his or her limb from the socket again, the patient merely needs to slide the air-transfer stem 164 back to the open position as shown in FIG. 7 so that air can be easily received back within the socket interior as the patient pulls his or her residual limb back out through the socket interior.

The present embodiment 158 of the valve plate assembly also provides for the coupling of a pump thereto (a needle at the end of a pump hose can be inserted into the first opening 167 in the air-transfer stem) so as to facilitate the forced transfer of air into and out from the socket interior 118 when the air-transfer stem 164 is in the open position as shown in FIG. 7.

Having described the invention in detail and by reference to the drawings, it will be apparent that modifications and variations are possible without departing from the scope of the invention as defined in the following claims.

What is claimed is:

1. A prosthetic limb comprising:
   a prosthetic limb socket shaped for receiving a patient's residual limb, the socket having a socket wall, a socket interior, a proximal opening, and a distal end;
   an upright assembly; and
   a valve assembly including,
      a base having a first surface and a second surface, fitted within the socket interior at the distal end of the socket, wherein said first surface faces the socket interior and the second surface faces the socket wall, wherein the base includes a channel extending therethrough providing fluid communication between the first surface and the second surface;
      a coupler, carried on the base, releasably attaching the upright assembly to the distal end of the socket and to the base;
      a valve extending through the socket and coupled to the base for controlling the flow of air from the socket interior and through the channel; and
      an O-ring member extending from the second surface of the base and providing an air-tight seal between the base and the socket wall.

2. The prosthetic limb of claim 1, further comprising:
   a cushion carried on the base, having a proximate end and a distal end, the proximate end being adapted to abut a wearer's residual limb.

3. The prosthetic limb of claim 2, wherein the cushion is formed from an elastomeric material and the cushion includes the O-ring member.

4. The prosthetic limb of claim 1, wherein the valve is a check valve.

5. The prosthetic limb of claim 1, wherein the base includes a second coupler releasably mounting the base within the socket interior.

6. The prosthetic limb of claim 5, wherein the first and the second couplers include a screw- or bolt-receiving hole extending into the base.

7. The valve assembly of claim 6, wherein the screw- or bolt-receiving hole is threaded.

8. A prosthetic limb, comprising:
   a prosthetic limb socket including a socket wall,
      a socket interior configured to contain a patient's residual limb,
      a proximal opening, and
      a distal end;
   an upright assembly;
   a base removably coupled to the distal end of the socket, the base including a channel extending therethrough and opening into the socket interior;
   a coupler, carried on the base, releasably attaching the upright assembly to the distal end of the socket; and
   a valve coupled to the base for controlling the flow of air through the channel.

9. The prosthetic limb of claim 8, further comprising an O-ring member extending from the base and providing an air-tight seal between the base and the socket wall.

10. A prosthetic limb, comprising:
    a prosthetic limb socket shaped for receiving a patient's residual limb, the socket having a socket wall, a socket interior, a proximal opening, and a distal end;
    an upright assembly;
    a base-plate fitted within the socket interior at the distal end of the socket, the base-plate including a channel extending into the base and opening onto the socket interior;
    a valve extending through the socket wall and coupled to the base-plate for controlling the flow of air from the socket interior and through the channel; and
    a bolt extending from the upright assembly, through the socket wall and into the base-plate;
    whereby the base-plate facilitates the passage of air from the socket interior and also facilitates the coupling of the upright assembly to the socket.

11. The prosthetic limb of claim 10, further comprising an air-tight seal between the base-plate and the socket wall.

12. A prosthetic limb, comprising:
    a prosthetic limb socket shaped for receiving a patient's residual limb, the socket having a socket wall, a socket interior, a proximal opening, and a distal end;
    a base-plate fitted within the socket interior at the distal end of the socket, the base-plate including a channel extending into the base-plate and opening onto the socket interior; and
    a port communicating with the channel, the port facilitating the coupling of a pump thereto so as provide a forced transfer of air to or from the socket interior.

13. A prosthetic limb, comprising:
    a socket having an interior configured to contain wear's residual limb, a distal end, and an inner surface;
    a valve assembly removably coupled to the distal end of the socket, providing fluid communication between the socket interior and the ambient; and
    an upright assembly removably coupled to the distal end of the valve assembly.

14. The prosthetic limb of claim 13, wherein the valve assembly includes an opening in fluid communication with the socket interior and an O-ring member surrounding the opening and providing an airtight seal between the valve assembly and the socket.

15. The prosthetic limb of claim 13, wherein the valve assembly includes a base member having a plurality of bolt receiving holes facilitating the removable coupling of the valve assembly to the distal end of the socket.

16. The prosthetic limb of claim 13, wherein the valve is a check valve allowing air to be released from the socket interior to the ambient while preventing air flow from the ambient back into the socket interior.

17. A prosthetic limb socket configured to receive a residual limb, said prosthetic limb socket comprising:
    a proximal opening;
    a socket wall and a distal end configured to define a socket interior,
    said distal end comprising a releasably attached base including
    a channel configured to conduct fluid between said socket interior and an exterior of said prosthetic limb socket, and
    a check valve located along said channel and configured to spontaneously open said channel in response to a socket interior pressure higher than an exterior pressure and close said channel in response to said socket interior pressure substantially equal to and less than said exterior pressure.

18. The prosthetic limb socket of claim 17, wherein said releasably attached base is fitted within said socket interior, sealed to said socket wall, and includes said channel and check valve contained therein.

19. The prosthetic limb socket of claim 17, wherein said check valve comprises means for allowing fluid flow to occur in substantially only a single direction.

20. The prosthetic limb device of claim 18, wherein said releasably attached base further comprises a porous pad component configured to pass fluid between said channel and said socket interior.

21. A device comprising:
   a prosthetic limb socket having a socket wall and a releasably attached base plate at a distal end of said prosthetic limb socket that define a prosthetic limb socket interior, said prosthetic limb socket interior configured to contain a residual limb therein;
   a channel located within said releasably attached base plate and configured to conduct fluid between said prosthetic limb socket interior and a prosthetic limb socket exterior and located within said releasably attached base plate; and
   a valve located along said channel and configured to seal and open said channel.

22. The device of claim 21, wherein said valve further comprises a check valve configured to substantially open in response to a positive pressure between said prosthetic limb socket interior and said prosthetic limb socket exterior and to substantially close in response to a at least one of a negative pressure and an equal pressure between said prosthetic limb socket interior and said prosthetic limb socket exterior.

23. The device of claim 21, wherein said valve is located within said releasably attached base plate.

24. The device of claim 21, further comprising:
   a valve plate component attached to said releasably attached base plate and further defining said channel.

25. The device of claim 24, wherein said valve is located within said valve plate component.

26. The device of claim 21, further comprising:
   a linking plate configured to be attached to said releasably attached base plate and to an upright member and further define said channel.

27. The device of claim 26, wherein said valve is at least partially located within said linking plate.

28. The device of claim 21, further comprising:
   an interface cushion configured to distribute a contact load when said residual limb is located within said prosthetic limb socket.

29. The device of claim 28, wherein said interface cushion comprises a porous pad member configured to further define said channel.

30. The device of claim 21, wherein said releasably attached base plate further comprises:
   an O-ring configured to seal said base to said socket wall.

31. The device of claim 21, wherein said releasably attached base plate further comprises:
   a coupler configured to releasably attach said prosthetic limb socket to an upright assembly.

32. The device of claim 21, further comprising a port in fluid communication with said channel and configured to facilitate attachment to a pump.

33. A device, comprising:
   means for receiving a residual limb;
   means for attaching said means for receiving and an upright assembly, said means for attaching being releasably attached to said means for receiving and including
   means for transporting fluid between an interior of said means for receiving and an exterior of said means for receiving.

* * * * *